United States Patent [19]
Afriat et al.

[11] Patent Number: 5,830,449
[45] Date of Patent: *Nov. 3, 1998

[54] STABLE COMPOSITION CONTAINING AN ENZYME

[75] Inventors: Isabelle Afriat, Paris; Didier Gagnebien, Chatillon, both of France

[73] Assignee: L'Oreal, Paris, France

[ * ] Notice: The term of this patent shall not extend beyond the expiration date of Pat. No. 5,703,041.

[21] Appl. No.: 686,922

[22] Filed: Jul. 24, 1996

[30] Foreign Application Priority Data

Jul. 25, 1995 [FR] France .................................. 95 09027

[51] Int. Cl.$^6$ .............................. A61K 31/78; A61K 7/48
[52] U.S. Cl. .................................... 424/78.02; 514/772.6; 424/401
[58] Field of Search ................................ 424/78.02, 401, 424/458; 514/772.6

[56] References Cited

U.S. PATENT DOCUMENTS

| | | | |
|---|---|---|---|
| 4,711,739 | 12/1987 | Kandathill | 252/139 |
| 5,133,968 | 7/1992 | Nakayama et al. | |
| 5,154,916 | 10/1992 | Arraudeau et al. | |
| 5,204,093 | 4/1993 | Victor | |
| 5,219,561 | 6/1993 | Gagnebien et al. | |
| 5,322,683 | 6/1994 | Mackles et al. | |
| 5,356,800 | 10/1994 | Jaquess | |
| 5,573,768 | 11/1996 | Afriat et al. | |

FOREIGN PATENT DOCUMENTS

| | | |
|---|---|---|
| A-0 550 279 | 7/1993 | European Pat. Off. |
| A-0 586 303 | 3/1994 | European Pat. Off. |
| A-0 623 342 | 11/1994 | European Pat. Off. |
| A 2 287 899 | 5/1976 | France |
| Hei 1-283213 | 5/1988 | Japan |
| A-61 123 | 8/1970 | Luxembourg |
| 1 255 284 | 12/1971 | United Kingdom |

OTHER PUBLICATIONS

Patent Abstracts of Japan, vol. 14, No. 57 (C–0684) Nov. 14, 1989 & JP–A–01 283213.

Patent Abstracts of Japan, vol. 14, No. 453 (C–0764) Jul. 11, 1990, & JP–A–02 178210.

CA 87:66843.

Tzanos, *Riv. Ital. Essenze, Profumi, Painte Off.*, vol. 59, No. 5, pp. 208–211 (1977).

D. Tzanos, "Enzyme Performance Through Control of Water Activity in the Medium—Description of a Practical Case–", Rivista Italiana Essenze, vol. 59, No. 5, pp. 208–211, 1977, with certified English translation.

Takashi Kinoshita et al., "Topical Formulations Containing a Pyridinecarboxylate Derivative as a Calcium Antagonist," Chemical Abstracts, vol. 109, No. 18, 156265v, Oct. 31, 1988.

Takashi Suzuki et al., "Topical Formulation Containing Urea", Chemical Abstracts, vol. 106, No. 4, p. 303, 23304y, Jan. 26, 1987.

Hiroshi Yamaguchi et al., "Topical Compositions for Treatment of Skin Diseases", Chemical Abstracts, vol. 106, No. 18, p. 370, 143995w, May 4, 1987.

*Primary Examiner*—Thurman K. Page
*Assistant Examiner*—P. Kulkosky
*Attorney, Agent, or Firm*—Oblon, Spivak, McClelland, Maier & Neustadt, P.C.

[57] ABSTRACT

A stable composition for topical application is provided which contains at least one enzyme, at least one polyol, the latter being present in a quantity which is effective for obtaining a water activity value of the composition of less than or equal to 0.85, and at least one structuring agent chosen from polymers and oils, for the purpose of stabilizing the enzyme. In such a composition, the enzyme retains its efficacy over time. The composition obtained can be used for cleansing and/or caring for and/or protecting the skin and/or keratinous fibers.

21 Claims, No Drawings

STABLE COMPOSITION CONTAINING AN ENZYME

BACKGROUND OF THE INVENTION

1. Field of the Invention

The subject of the present invention is a composition for topical application containing an enzyme intended to be used, in particular, in order to cleanse and/or care for and/or protect the skin and/or keratinous fibers.

2. Discussion of the Background

It is known to introduce, into cosmetic and/or dermatological compositions, enzymes and in particular proteases used for their proteolytic properties. These enzymes are sought after in the cosmetics field for their smoothing and cleansing power and their ability to remove dead cells from the skin.

Unfortunately, enzymes have the disadvantage of being unstable in aqueous medium and of being readily degraded or modified under the influence of water. They rapidly lose their activity over time, and this instability goes against the desired efficacy.

Various means have therefore been envisaged for overcoming this disadvantage. In particular, the incorporation of an enzyme into a pulverulent composition has been envisaged (see JP-A-63-130514). Moreover, the majority of skin cleansing products are in this form. It has also been envisaged to use enzymes in a form immobilized on polymeric supports (see JP-A-61-207499) or in microcapsules (see JP-A-61-254244). Unfortunately, some of these means necessitate a special procedure, which increases the cost and time associated with the preparation of the composition.

Another solution involves in incorporating the enzymes into an anhydrous liquid medium (see U.S. Pat. No. 5,322,683). Unfortunately, this solution limits the pharmaceutical form of the composition and does not permit the incorporation of hydrophilic active principles.

There is, therefore, still a need for a composition for a topical application containing enzymes, in which the latter retain all of their properties and, therefore, their efficacy over time.

SUMMARY OF THE INVENTION

It has now been found, unexpectedly, that the use of at least one water-binding polyol in a topical composition containing an enzyme, in a quantity which is effective for obtaining a water activity value of the composition of less than or equal to 0.85, and of at least one structuring agent makes it possible to avoid the degradation of the enzyme.

DETAILED DESCRIPTION OF THE PREFERRED EMBODIMENTS

The present invention relates to a stable composition for topical application containing at least one enzyme and at least one polyol, characterized in that the composition contains no calcium salt, the polyol is present in a quantity which is effective for obtaining a water activity value of the composition of less than or equal to 0.85, and the composition contains at least one structuring agent chosen from polymers and oils.

The invention also relates to a stable composition for topical application containing at least one enzyme and at least one polyol, characterized in that the polyol is present in a quantity ranging from 30 to 99.99% by weight, relative to the total weight of the composition, and the composition comprises at least one structuring agent chosen from acrylic polymers, methacrylic polymers and oils.

Admittedly, it is known that the water content can have an influence on the stability of enzymes, but it has never been described nor suggested that the presence alone of polyol and of a structuring agent might prevent their degradation. Thus the article by D. Tzanos "Behavior of enzymes by controlling the medium water activity"; Riv. Ital. Essenze, Profumi, Piante Off., Aromi, Saponi, Cosmet., Aerosol, 1977, vol. 59, No. 5, pages 208–211, encourages a person skilled in the art to use surfactants for stabilizing enzymes in aqueous medium or to attach the enzymes to a porous support. It leads the person skilled in the art away from using glycols.

Moreover, U.S. Pat. No. 5,356,800 describes a process for stabilizing enzymes which involves using a mixture of an alcohol or a glycol, an oxyethylenated alkyldiamine and an amine oxide. According to this article, the enzymes can only be stabilized by using the described mixture.

In addition, JP-A-01-283213 describes a cleansing composition containing an enzyme and a polyol. According to this document, the enzymatic activity is stabilized by addition of a protein such as collagen, elastin or albumin.

FR-A-1,397,399 describes a process for stabilizing proteases which involves using a mixture of polyol and of a calcium salt. According to this document, the presence of calcium salt is essential for the stabilization of the protease.

Moreover, it is known from J. Soc. Cosm. Chem. Jap., 1993 27(3), p. 276–288, that it is possible to stabilize proteases by chemically modifying them and that the addition of polyols contributes to improving the stability of the modified protease. According to this document, chemical modification is necessary in order to obtain stabilization of the enzymes.

It has now been found that, in the case of topical compositions, polyols used in a sufficient quantity and in combination with a structuring agent are able to prevent the degradation of water-sensitive active agents.

The present invention relates further to the use, in a composition for topical application which contains no calcium salt and contains at least one enzyme, of at least one polyol in a quantity which is effective for obtaining a water activity value of the composition of less than or equal to 0.85, and of at least one structuring agent chosen from polymers and oils, for the purpose of stabilizing the enzyme. The polymer is preferably chosen from acrylic and methacrylic polymers.

The quantity of the polyol or polyols should preferably be such that the water activity value of the composition is less than or equal to 0.7.

The water activity $a_w$ of a medium containing water is the ratio of the water vapor pressure of the product "$P_{H_2O}$ product" to the vapor pressure of pure water "$P_{H_2O}$ pure" at the same temperature. It can also be expressed as the ratio of the number of molecules of water "$N_{H_2O}$" to the total number of molecules "$N_{H_2O}+N_{dissolved\ substances}$", which takes account of the molecules of dissolved substances "$N_{dissolved\ substances}$".

It is given by the following formulae:

$$a_w = \frac{P_{H_2O}\ \text{product}}{P_{H_2O}\ \text{pure}} = \frac{N_{H_2O}}{N_{H_2O} + N_{dissolved\ substances}}$$

Various methods can be used for measuring the water activity. The most common is the manometric method, by which the vapor pressure is measured directly.

Conventionally, a cosmetic or dermatological composition has a water activity of about 0.95 to 0.99. A water activity of less than 0.85 represents a considerable reduction in the water activity.

The polyol used according to the invention can in particular be chosen from glycerol and glycols, preferably poly($C_{2-4}$ alkylene) glycols and glycols containing 3–10 carbon atoms, in particular propylene glycol and polyethylene glycols. Preferred polyethylene glycols have a weight average molecular weight in the range from about 50 to about 600 g/mole.

The quantity of the polyol or polyols to be used is dependent on the type of compositions (gel or emulsion) and on the other constituents of the composition. This quantity must be sufficient to achieve a suitable water activity. The polyol or polyols used according to the invention are preferably present in a quantity of at least 30% by weight, preferably ranging from 30 to 99.99% by weight, and more preferably from 60 to 80% by weight, relative to the total weight of the composition.

According to a preferred embodiment of the invention, the polyol or polyols is or are totally or partially present as a complex with an acrylic or methacrylic polymer. The polymer may also comprise bound water, i.e. can be complexed with a mixture of water and polyol(s).

The term acrylic or methacrylic polymer refers to a homopolymer or a copolymer of acrylic or methacrylic acid or a homopolymer or a copolymer of a derivative of acrylic or methacrylic acid. Preferred acrylic and methacrylic acid derivatives are the esters of these acids with suitable alcohols containing, for example, 1–10 carbon atoms and 1 or more, preferably 1–3 hydroxyl groups. The amount of acrylic or methacrylic acid in the copolymer can be widely varied and is not particularly limiting so long as the properties of the composition of the invention are retained.

The quantity of polymers with the polyol or polyols and, if appropriate, the bound water in the composition according to the invention preferably ranges from 70 to 99.99% by weight, more preferably from 80 to 95% by weight, relative to the total weight of the composition.

As homopolymers which complex water and polyols, those sold under the names NORGEL and LUBRAJEL CG by Guardian may be mentioned. These polymers are poly (glyceryl acrylate)s complexed with more than 65% of glycerol and/or of propylene glycol and less than 35% by weight of water. These polymers provide the complexed water and polyol and may additionally play the part of a gelling agent for the composition.

The comparative tests presented below show that only compositions having a bound water activity value of no more than 0.85 enable effective retention of the enzymatic activity of the enzymes.

The enzymes used according to the invention are preferably lactoperoxidases, lipases, proteases, phospholipases and cellulases. The enzyme or enzymes used according to the invention is more preferably a protease. They can be chosen, for example, from that sold under the trade name SUBTILISIN SP 544 by Novo Nordisk and that sold under the trade name LYSOVEG by Laboratoires Sérobiologiques de Nancy.

In the composition according to the invention, the enzyme is preferably used in a quantity ranging from 0.001 to 15% by weight, more preferably from 0.01 to 10% by weight and, even more preferably, from 0.05 to 5% by weight, relative to the total weight of the composition.

As oils which can be used in the invention, mention may be made of mineral oils (liquid petroleum), vegetable oils (jojoba oil), animal oils, synthetic oils (decyl oleate), silicone oils (cyclomethicone, polydimethylsiloxane, dimethicone) and fluorinated oils (perfluoropolyethers). The oil or oils can be present in a quantity ranging from 5 to 60%, and preferably from 5 to 40%, by weight relative to the total weight of the composition.

In addition, the composition according to the invention may contain one or more salts whose presence will further improve the stability of the active agent present therein. Salts which may be mentioned in particular are magnesium salts and sodium salts and more especially magnesium sulphate, magnesium chloride and sodium chloride. The salt or salts may be present in a quantity ranging from 0.1 to 30% and preferably from 2 to 12% by weight, relative to the total weight of the composition.

The composition according to the invention contains a medium which is topically acceptable, i.e. compatible with the skin and hair, and in particular constitutes compositions for cleansing, protection, treatment or care of the skin and/or hair, in particular for the face, neck, hands, hair, scalp or body, as well as for the eyelashes.

In addition, a further subject of the invention is the use of the composition according to the invention for cleansing and/or protecting the skin and/or keratinous fibers, i.e. the hair and/or eyelashes.

The present invention also relates to a cleansing composition for the skin and/or the keratinous fibers which contains at least one enzyme and at least one polyol, characterized in that the composition contains no calcium salt, the polyol is present in a quantity which is effective for obtaining a water activity value of the composition of less than or equal to 0.85, and in that the composition contains at least one structuring agent chosen from polymers and oils.

Finally, the invention relates to a cosmetic and/or dermatological method of cleansing and/or protecting the skin and/or keratinous fibers, by applying to the skin and/or keratinous fibers a composition which contains no calcium salt and contains at least one enzyme, at least one polyol present in a quantity which is effective for obtaining a water activity value of the composition of less than or equal to 0.85 for the purpose of stabilizing the enzyme, and at least one structuring agent chosen from polymers and oils.

The composition according to the invention can be provided in particular in the form of a solution, a gel or a water-in-oil or oil-in-water emulsion constituting creams, ointments, lotions or milks. This composition can also comprise microcapsules, microparticles or vesicular dispersions of ionic and/or nonionic type. These various forms of composition are prepared according to the usual methods.

These compositions constitute, in particular, creams for the protection, treatment or care of the face, hands or feet, body milks for protection or care or lotions, gels or mousses for the care of the skin, hair, mucosae and scalp.

When the composition of the invention is an emulsion, the proportion of the fatty phase can range from 10% to 80% by weight, and preferably from 20% to 40% by weight, relative to the total weight of the composition. The emulsion preferably comprises at least one dispersant chosen from emulsifiers, vesicles and particles. The oils, the emulsifiers and optionally the co-emulsifiers used in the composition in emulsion form are chosen from those conventionally used in the cosmetics and dermatological fields. The emulsifier and the co-emulsifier are, for example, present in the composition in a proportion ranging from 1% to 10% by weight, and preferably from 2 to 6% by weight, relative to the total weight of the composition.

In a known manner, the composition of the invention may additionally contain adjuvants usual in the cosmetics and dermatological fields, such as surfactants, in particular foaming surfactants, hydrophilic or lipophilic active agents, preservatives, antioxidants, solvents, fragrances, fillers, screening agents, odor absorbers and coloring substances. The quantities of these various adjuvants are those conventionally used in the fields under consideration and are, for example, from 0.01% to 10% by weight of the total weight of the composition. These adjuvants, depending on their nature, can be introduced into the fatty phase, into the aqueous phase and/or into the lipid vesicles.

In addition to the abovementioned oils, the fatty phase may comprise fatty substances such as fatty alcohols, fatty acids (stearic acid) or waxes (silicone wax).

As foaming surfactants which can be used in the invention, mention may be made of disodium cocoamphodiacetate (MIRANOL C2M sold by Rhône-Poulenc) and the decyl ether of glucose at 55% concentration in water (ORAMIX NS10 sold by the company Seppic). The water content of these starting materials forms part of the total quantity of water in the composition.

As emulsifiers which can be used in the invention, mention may be made of, for example, silicone emulsifiers, for instance alkyldimethicone copolyols, such as the cetyldimethicone copolyol sold by Goldschmidt under the name ABIL EM-90 or the mixture of dimethicone copolyol and cyclomethicone sold by Dow Corning under the name 3225C FORMULATION AID.

As hydrophilic active agents it is possible to use proteins or protein hydrolysates, amino acids, urea, allantoin, sugars and sugar derivatives, water-soluble vitamins, starch or bacterial or plant extracts, in particular aloe vera.

As lipophilic active agents it is possible to use tocopherol (vitamin E) and derivatives thereof, retinol (vitamin A) and derivatives thereof, essential fatty acids, ceramides and essential oils.

EXAMPLES

Test for stability of enzymatic activity:

The enzymatic activity of an enzyme present in an aqueous gel according to the invention and in two comparative gels was determined using the casein method. According to this method, the casein used as substrate is hydrolysed by the enzyme, releasing amino acids which are then quantified calorimetrically using Folin-Ciocalteu's reagent. The calorimetric absorbance read off is larger the greater the quantity of enzyme.

The gels tested contained 1% w/w of protease (protease SP 544) and had the following composition:

Gel I (according to the invention): 99% of NORGEL (i.e. 0.99% of acrylic polymer, 66.3% of polyol and 30.7% of water) and 1% of protease.

Gel II (comparative): 99% of propylene glycol alginate with a degree of esterification of 80–85%, at a concentration of 0.5% in water, and 1% of protease.

Gel III (comparative): 99% of polysaccharide (FUCOGEL 1000: biosaccharide gum-1 sold by Solabia, based on fucose, galactose and galacturonic acid) and 1% of protease.

The following table gives the results in terms of the percentage enzymatic activity remaining after two months:

| Gel | Water activity of the gel $a_w$ | % enzymatic activity |
| --- | --- | --- |
| Gel I | 0.65 | 71% |
| Gel II | 0.989 | 0% |
| Gel III | 0.967 | 0% |

These results show that only gel I according to the invention allows the enzymatic activity of the protease to be conserved.

The examples which follow of compositions according to the invention are given by way of illustration and are not limiting. The quantities given therein are in % by weight.

Example 1

Gel

NORGEL 85%
SUBTILISIN SP 544 0.1%
Water up to 100%

A translucent gel was obtained which can be used as an exfoliating gel. The water activity was 0.735±0.05. After 2 months at room temperature, the enzymatic activity of the Subtilisin SP 544 was still 80%.

Example 2

Water-in-Oil Emulsion

| (a) Aqueous phase: | |
| --- | --- |
| NORGEL | 71.5% |
| NaCl | 0.5% |
| Water | up to 100% |
| (b) Oily phase: | |
| Cetyldimethicone copolyol (ABIL EM-90 sold by Goldschmidt) (emulsifier) | 2% |
| Jojoba oil | 4% |
| Liquid petroleum | 10% |
| Polydimethylsiloxane | 8% |
| Decyl oleate | 3.9% |
| SUBTILISIN SP 544 | 0.1% |

The procedure for preparing the emulsion was as follows: the aqueous phase was prepared on the one hand and the oily phase on the other hand, and the aqueous phase was emulsified in the oily phase at room temperature with stirring using a homogenizer.

A white cream was obtained which was capable of facilitating removal of skin cells and lightening the complexion. The water activity was 0.62±0.02. After 2 months at room temperature, the enzymatic activity of the SUBTILISIN SP 544 was still 100%.

Example 3

Cleansing Gel

| SUBTILISIN SP 544 | 0.04% |
| --- | --- |
| NORGEL | 83% |
| MIRANOL C2M (sold by Rhône-Poulenc) | 16% |
| Water | 100% |

A foaming cleansing gel for the face and body was obtained which can be rinsed off with water. The water activity was 0.67—0.02.

Example 4

Cleansing Gel

| | |
|---|---|
| NORGEL | 88.97% |
| LYSOVEG | 0.03% |
| ORAMIX NS10 (sold by Seppic) | 11% |

A foaming cleansing gel for the face and body was obtained which can be rinsed off with water. The water activity was 0.68±0.02.

Example 5

Water-in-Oil Emulsion

| | |
|---|---|
| (a) Oily phase: | |
| Dimethicone copolyol and cyclomethicone ("3225C FORMULATION AID" sold by Dow Corning) | 22.6% |
| Dimethicone | 5% |
| Mineral oil | 3% |
| (b) Aqueous phase: | |
| Glycerol | 45.5% |
| SUBTILISIN SP 544 | 0.05% |
| Magnesium sulphate (stabilizer) | 2% |
| Propylene glycol | 8% |
| Water | up to 100% |

The emulsion was prepared as in Example 2. A white cream for smoothing the skin was obtained, the water activity of which was 0.63±0.02. After 2 months at room temperature, the enzymatic activity of the SUBTILISIN SP 544 was still 90%.

Example 6

Water-in-Oil Emulsion

| | |
|---|---|
| (a) Oily phase: | |
| Dimethicone copolyol and cyclomethicone ("3225C FORMULATION AID" sold by Dow Corning) | 22.8% |
| Dimethicone | 5% |
| Octyl palmitate | 6.7% |
| Corn starch | 8% |
| nylon-12 | 5% |
| (b) Aqueous phase: | |
| Glycerol | 8% |
| Propylene glycol | 8% |
| Magnesium chloride | 6% |
| SUBTILISIN SP 544 | 0.1% |
| Water | up to 100% |

The emulsion was prepared as in Example 2. A white cream for smoothing the skin was obtained, the water activity of which is 0.75±0.02.

French Priority Document FR 95-09027 is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A composition for topical application to the body, comprising:
   water,
   0.001 to 15% by weight of at least one enzyme,
   at least 30% by weight of at least one polyol, and
   at least about 0.71% by weight of at least one structuring agent selected from the group consisting of a homopolymer of acrylic acid, a homopolymer of methacrylic acid, a copolymer of acrylic acid and methacrylic acid, a copolymer of acrylic acid and an methacrylic acid ester and a copolymer of an acrylic acid ester and methacrylic acid,
   wherein the composition
      comprises, in total, 70 to 99.99% by weight of the water, polyol and the structuring agent,
      has a water activity of at most 0.85, and
      contains no calcium salt.

2. The composition of claim 1, wherein the enzyme is non-microencapsulated.

3. The composition of claim 2, wherein the acrylic polymer or methacrylic polymers is complexed with a polyol.

4. The composition of claim 2, wherein the structuring agent is a poly(glyceryl acrylate).

5. The composition of claim 2, wherein the structuring agent is a poly(glyceryl acrylate) complexed with a polyol.

6. The composition of claim 5, wherein the poly(glyceryl acrylate) is complexed with a polyol selected from the group consisting of glycerol, propylene glycol and mixtures thereof.

7. The composition of claim 1, wherein the acrylic polymer or methacrylic polymer is complexed with a polyol.

8. The composition of claim 1, wherein the structuring agent is a poly(glyceryl acrylate).

9. The composition of claim 1, wherein the structuring agent is a poly(glyceryl acrylate) complexed with a polyol.

10. The composition of claim 9, wherein the poly(glyceryl acrylate) is complexed with a polyol selected from the group consisting of glycerol, propylene glycol and mixtures thereof.

11. The composition of claim 1, wherein the polyol is selected from the group consisting of glycerol and glycols.

12. The composition of claim 1, having a water activity of at most 0.7.

13. The composition of claim 1, wherein the enzyme is a protease.

14. The composition of claim 1, further comprising a magnesium salt or a sodium salt.

15. The composition of claim 1, further comprising at least one lipophilic or hydrophobic adjuvant selected from the group consisting of preservatives, antioxidants, fragrances, fillers, screening agents, sequestering agents, essential oils, coloring substances, hydrophilic or lipophilic active agents and lipid vesicles.

16. The composition of claim 1, which is an emulsion and further comprises at least one dispersant selected from the group consisting of emulsifiers, vesicles and particles.

17. A method of cleansing and/or protecting the skin and/or keratinous fibers, comprising applying an effective amount of the composition of claim 1 to skin and/or keratinous fibers in need thereof.

18. A composition for topical application to the body, comprising:
   water,
   0.001 to 15% by weight of at least one enzyme,
   at least 30% by weight of at least one polyol selected from the group consisting of glycerol, poly(alkylene) glycols and glycols having 3 to 10 carbon atoms, and 5 to 60% by weight of at least one oil selected from the group consisting of mineral oils, vegetable oils, animal oils, synthetic oils, silicone oils and fluorinated oils, and wherein the composition has a water activity of at most 0.85 and contains no calcium salt.

19. The composition of claim 18, wherein the enzyme is non-microencapsulated.

20. The composition of claim 18, wherein the enzyme is a protease.

21. A method of cleansing and/or protecting the skin and/or keratinous fibers, comprising applying an effective amount of the composition of claim 18 to skin and/or keratinous fibers in need thereof.

* * * * *